(12) United States Patent
Wear et al.

(10) Patent No.: US 12,727,843 B2
(45) Date of Patent: Sep. 8, 2026

(54) SYSTEM AND METHOD FOR MANUFACTURING AN X-ray BONE PHANTOM

(71) Applicant: GE Precision Healthcare LLC, Waukesha, WI (US)

(72) Inventors: James A. Wear, Madison, WI (US); Jaroslaw Jarek Kurzac, Oconomowoc, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 115 days.

(21) Appl. No.: 18/913,110

(22) Filed: Oct. 11, 2024

(65) Prior Publication Data

US 2026/0102135 A1 Apr. 16, 2026

(51) Int. Cl.

| | |
|---|---|
| ***A61B 6/58*** | (2024.01) |
| ***B22F 10/80*** | (2021.01) |
| ***B33Y 50/00*** | (2015.01) |
| ***B33Y 70/00*** | (2020.01) |
| ***B33Y 80/00*** | (2015.01) |
| ***G06F 30/17*** | (2020.01) |
| ***G06F 113/10*** | (2020.01) |
| ***G09B 23/28*** | (2006.01) |

(52) U.S. Cl.

CPC .............. *A61B 6/583* (2013.01); *B22F 10/80* (2021.01); *B33Y 50/00* (2014.12); *G06F 30/17* (2020.01); *G09B 23/286* (2013.01); *B33Y 70/00* (2014.12); *B33Y 80/00* (2014.12); *G06F 2113/10* (2020.01)

(58) Field of Classification Search

CPC ...................................................... A61B 6/583

See application file for complete search history.

(56) References Cited

U.S. PATENT DOCUMENTS

| | | | | |
|---|---|---|---|---|
| 10,254,499 | B1 * | 4/2019 | Cohen | G02B 6/25 |
| 2016/0271379 | A1 * | 9/2016 | Pouliot | A61B 6/037 |
| 2017/0291359 | A1 * | 10/2017 | Kerins | B29C 37/0025 |

(Continued)

OTHER PUBLICATIONS

Karaman et al., "Utilizing Additive Manufacturing to Produce Organ Mimics and Imaging Phantoms," MDPI, Surgeries, 2023, 15 pgs.

(Continued)

*Primary Examiner* — Edwin C Gunberg
(74) *Attorney, Agent, or Firm* — Fletcher Yoder, P.C.

(57) ABSTRACT

A computer-implemented method for manufacturing an X-ray bone phantom is provided. The computer-implemented method includes obtaining, via a processing system comprising one or more processors, dual-energy scan data from one or more dual-energy scans of an ex vivo bone phantom. The computer-implemented method also includes converting, via the processing system, the dual-energy scan data into a two-dimensional image. The computer-implemented method further includes printing, via the processing system, a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

18 Claims, 10 Drawing Sheets

(56) References Cited

U.S. PATENT DOCUMENTS

| | | | | |
|---|---|---|---|---|
| 2018/0267127 | A1* | 9/2018 | Geiger | A61B 8/587 |
| 2025/0001697 | A1* | 1/2025 | Nimonkar | G16H 30/40 |

OTHER PUBLICATIONS

Ma et al., "Classification of X-Ray Attenuation Properties of Additive Manufacturing and 3D Printing Materials Using Computed Tomography From 70 to 140kVp," Frontiers in Bioengineering and Biotechnology, 2021, 13 pgs.

McGarry et al., "Tissue mimicking materials for imaging and therapy phantoms: a review," Physics in Medicine & Biology, Institute of Physics and Engineering in Medicine, 2020, 44 pgs.

Silvestro et al., "Imaging Properties of Additive Manufactured (3D Printed) Materials for Potential Use for Phantom Models," Journal of Digital Imaging, 2020, 9 pgs.

* cited by examiner

SYSTEM AND METHOD FOR MANUFACTURING AN X-ray BONE PHANTOM

BACKGROUND

The subject matter disclosed herein relates to manufacturing of an X-ray bone phantom.

The bone mineral density (BMD) of a bone reflects the strength of the bone as represented by calcium content. It is defined as the integral mass of bone mineral per unit of projected area in grams per square centimeter. BMD is a useful tool for the diagnosis and treatment of several diseases and conditions, one of which is osteoporosis.

Osteoporosis is a disease of bone in which the BMD is reduced due to depletion of calcium and bone protein. Osteoporosis predisposes a person to fractures, which are often slow to heal and heal poorly. It is more common in older adults, particularly post-menopausal women; in patients on steroids; and in those who take steroidal drugs. Unchecked osteoporosis can lead to changes in posture, physical abnormality (particularly a condition known colloquially as "dowager's hump"), and decreased mobility. Treatment of osteoporosis includes ensuring that the patient's diet contains adequate calcium and other minerals needed to promote new bone growth, and for post-menopausal women, estrogen or combination hormone supplements.

Dual-energy X-ray absorptiometry (DXA or DEXA) is an increasingly important bone density measurement technology. In fact, osteoporosis is defined by the World Health Organization (WHO) as a BMD having a value 2.5 standard deviations below peak bone mass (in a 20-year-old sex-matched healthy person average) as measured by DXA. The fundamental principle behind DXA is the measurement of the transmission of X-rays with two different energy levels. By measuring how much X-ray energy is transmitted through the patient, the amount of X-ray energy that is absorbed in the patient can be determined. Soft tissues and bone absorb the two energy level X-rays to different degrees. As a result, the absorption of X-rays by the soft tissue may be distinguished from the absorption of X-rays by bone. The soft tissue image data may then be subtracted from the bone image data, leaving only the image data for bone. The BMD is then determined from the bone image data.

In rare instances, osteoporosis drug therapy backfires and femurs develop stress fractures across the shaft. If undetected, this could result in an atypical femur fracture (AFF), where the shaft catastrophically snaps. Prior to AFF, the bone tries to patch the fracture by building a callous of extra bone called "beaks". Certain DXA systems can be configured to detect and quantify beak height from DXA femur scans. X-ray bone phantoms for AFF are hand-crafted using ex vivo bone and plaster and are utilized as local calibration tools for the DXA systems. However, the ability to provide these phantoms to different countries is restricted. In addition, these phantoms are fragile. Further, these phantoms may be limited in terms of the unique features presented for calibration.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the disclosed subject matter may encompass a variety of forms that may be similar to or different from the embodiments set forth below.

In one embodiment, a computer-implemented method for manufacturing an X-ray bone phantom is provided. The computer-implemented method includes obtaining, via a processing system including one or more processors, dual-energy scan data from one or more dual-energy scans of an ex vivo bone phantom. The computer-implemented method also includes converting, via the processing system, the dual-energy scan data into a two-dimensional image. The computer-implemented method further includes printing, via the processing system, a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

In an additional embodiment, a system for manufacturing an X-ray bone phantom is provided. The system includes a memory encoding processor-executable routines. The system also includes a processing system including one or more processors and configured to access the memory and to execute the processor-executable routines, wherein the process-executable routines, when executed by the processing system, cause the processing system to perform actions. The actions include obtaining dual-energy scan data from one or more dual-energy scans of an ex vivo bone phantom. The actions also include converting the dual-energy scan data into a two-dimensional image. The actions further include printing a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

In a further embodiment, a non-transitory computer-readable medium, the computer-readable medium including processor-executable code that when executed by a processing system including one or more processors, causes the processing system to perform actions. The actions include obtaining dual-energy scan data from one or more dual-energy scans of an ex vivo bone phantom. The actions also include converting the dual-energy scan data into a two-dimensional image. The actions further include printing a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
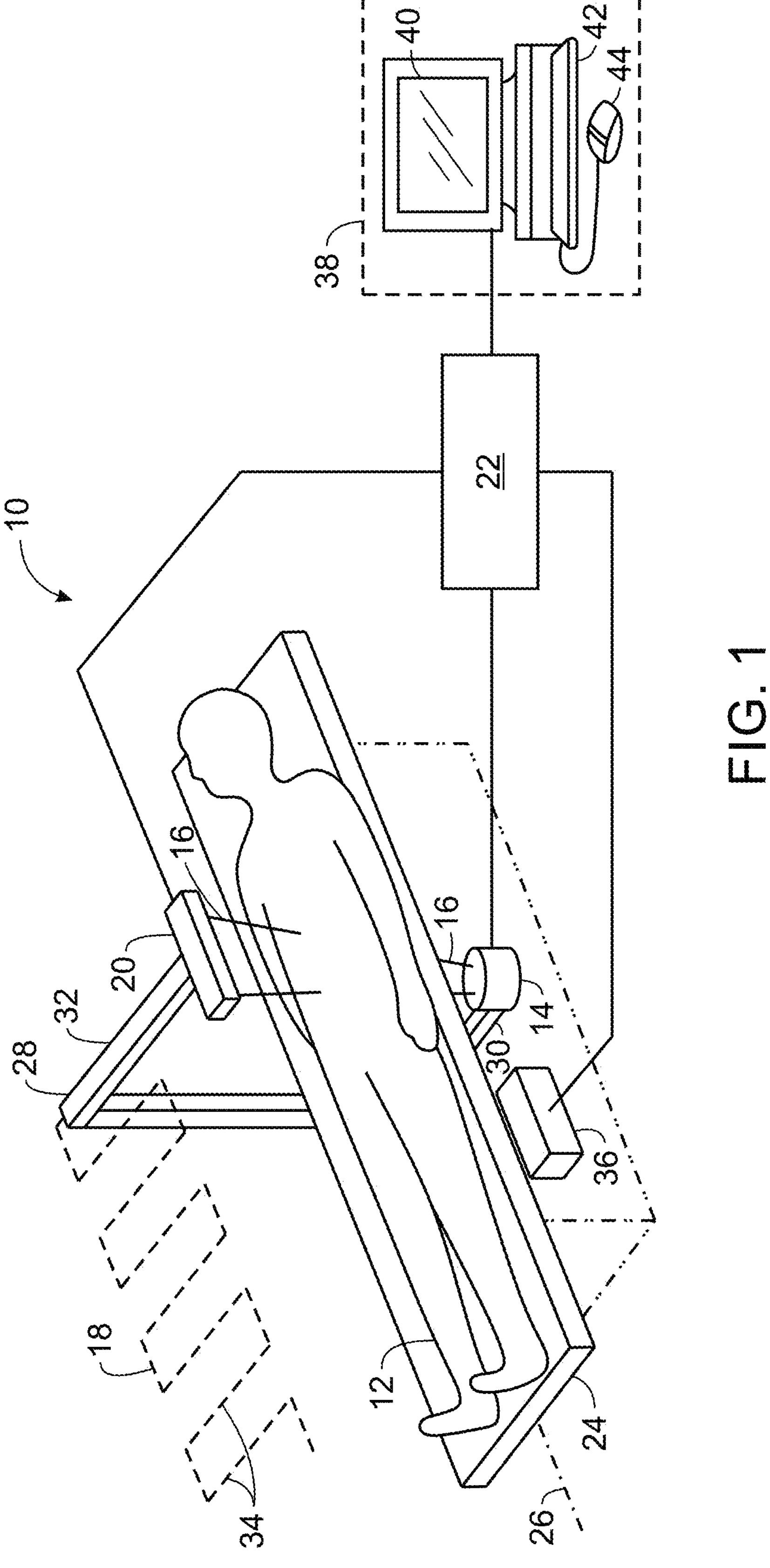
FIG. 1 is a perspective view of a system for a bone density scan of a patient, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided to provide both general context for aspects of the present disclosure and to facilitate understanding and explanation of certain of the technical concepts described herein.

The term processor, processing system, or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

As used herein, the term "computing system" refers to an electronic computing device such as, but not limited to, a single computer, virtual machine, virtual container, host, server, laptop, and/or mobile device, or to a plurality of electronic computing devices working together to perform the function described as being performed on or by the computing system. As used herein, the terms "application", "application module" (or "module"), "engine", or "program", or "plugin" refers to one or more sets of computer software instructions (e.g., computer programs and/or scripts) executable by one or more processors of a computing system to provide particular functionality. Computer software instructions can be written in any suitable programming languages, such as C, C++, C#, Pascal, Fortran, Perl, MATLAB, SAS, SPSS, JavaScript, AJAX, and JAVA. Such computer software instructions can comprise an independent application with data input and data display aspects (e.g., modules). Alternatively, the disclosed computer software instructions can be classes that are instantiated as distributed objects. The disclosed computer software instructions can also be component software, for example JAVABEANS or ENTERPRISE JAVABEANS. Additionally, the disclosed applications or engines can be implemented in computer software, computer hardware, or a combination thereof.

As used herein, the terms "automatic" and "automatically" refer to actions that are performed by a computing device or computing system (e.g., of one or more computing devices) without human intervention. For example, automatically performed functions may be performed by computing devices or systems based solely on data stored on and/or received by the computing devices or systems despite the fact that no human users have prompted the computing devices or systems to perform such functions. As but one non-limiting example, the computing devices or systems may make decisions and/or initiate other functions based solely on the decisions made by the computing devices or systems, regardless of any other inputs relating to the decisions.

The present techniques relate to various aspects of manufacturing an X-ray bone phantom. In particular, the present techniques provide for additive manufacturing (e.g., three-dimensional (3D) printing) of a topographic, semi-anthropomorphic X-ray bone phantom with calibrated attenuation properties. These additively manufactured X-ray bone phantoms may be two-dimensional (2D) or three-dimensional. The additively manufactured X-ray bone phantoms can be utilized to replace ex vivo bone phantoms that are unique and no longer readily available. The additively manufactured X-ray bone phantoms are made of aluminum as the bone mineral substitute (as opposed to other types of bone phantoms which utilize hydroxyapatite as the bone mineral substitute, which is not suitable for additive manufacturing). DXA imaging can utilize basis set decomposition using acrylic and aluminum as X-ray attenuation surrogates for soft tissue and bone mineral, respectively. The density of the additive aluminum in the additively manufactured may be tuned to ensure X-ray attenuation matches aluminum standards, which were calibrated to areal bone mineral density through standard DXA techniques.

The disclosed techniques may be utilized for any dual-energy application that relies on aluminum as part of their basis set enabling the use of additive phantoms in their calibration protocols. For example, the disclosed techniques may be utilized for security scanners for baggage.

The disclosed embodiments eliminate the use of ex vivo bone phantoms, which is desirable for both ethical and practical reasons (fragility of bones). The disclosed embodiments reduce the cost associated with manufacturing X-ray bone phantoms. The disclosed embodiments are easier to control and to handle compared to ex vivo bone phantoms. The disclosed embodiments provide an X-ray bone phantom with truly anthropomorphic attenuation properties at a fine scale. The disclosed embodiments enable the manufacture of unique X-ray bone phantoms that can be utilized to verify device performance for rare, outlier conditions.

The disclosed embodiments include a computer-implemented method for manufacturing an X-ray bone phantom that includes obtaining, via a processing system including one or more processors, dual-energy scan data from one or more dual-energy scans of an ex vivo bone phantom. The computer-implemented method also includes converting, via the processing system, the dual-energy scan data into a two-dimensional image. The computer-implemented method further includes printing, via the processing system, a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

In certain embodiments, the aluminum of the semi-anthropomorphic X-ray bone phantom is tuned to ensure an X-ray attenuation matches aluminum standards (e.g., of aluminum samples), wherein the aluminum standards were calibrated to areal bone density via dual-energy X-ray absorptiometry. In certain embodiments, the semi-anthropomorphic X-ray bone phantom is printed via an additive printer utilizing one or more parameter settings configured to correlate a thickness and a density of the aluminum to mimic bone shape and bone density and related X-ray attenuation.

In certain embodiments, the computer-implemented method further includes defining, via the processing system, an X-ray projection through the ex vivo bone phantom based on the dual-energy scan data and calculating, via the processing system, an aluminum equivalent of attenuating material along the X-ray projection. In certain embodiments, converting the dual-energy scan data into the two-dimensional image includes generating the two-dimensional image based on a thickness of the aluminum equivalent along the X-ray projection. In certain embodiments, the two-dimensional image includes a gray-scale bitmap with an amplitude proportional to the thickness of the aluminum equivalent. In certain embodiments, the computer-implemented method further includes modifying, via the processing system, the two-dimensional image to alter the thickness of the aluminum equivalent, wherein the semi-anthropomorphic X-ray bone phantom has one or more features different from the ex vivo bone phantom in morphology and/or areal bone mineral density.

In certain embodiments, the semi-anthropomorphic X-ray bone phantom is two-dimensional. In certain embodiments, the computer-implemented method further includes converting, via the processing system, the dual-energy scan data into a stack of two-dimensional images; and printing, via the processing system, the semi-anthropomorphic X-ray bone phantom made of aluminum based on the stack of two-dimensional images, wherein the semi-anthropomorphic X-ray bone phantom is three-dimensional.

The disclosed embodiments also include a system for manufacturing an X-ray bone phantom is provided. The system includes a memory encoding processor-executable routines. The system also includes a processing system including one or more processors and configured to access the memory and to execute the processor-executable routines, wherein the process-executable routines, when executed by the processing system, cause the processing system to perform actions. The actions include obtaining dual-energy scan data from one or more dual-energy scans of an ex vivo bone phantom. The actions also include converting the dual-energy scan data into a two-dimensional image. The actions further include printing a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

The disclosed embodiments further include a non-transitory computer-readable medium, the computer-readable medium including processor-executable code that when executed by a processing system including one or more processors, causes the processing system to perform actions. The actions include obtaining dual-energy scan data from one or more dual-energy scans of an ex vivo bone phantom. The actions also include converting the dual-energy scan data into a two-dimensional image. The actions further include printing a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

Referring now to FIG. 1, the major components of a system 10 for performing a bone density scan of an object/patient 12 are shown. As will be appreciated, in embodiments, the system 10 may be a dual-energy X-ray absorptiometry (DEXA or DXA) system that functions as a dual energy bone densitometer capable of performing bone densitometry. Accordingly, in embodiments, the bone density scan performed by the system 10 may be used to generate a bone mineral content (BMC) measurement, a bone mineral density (BMD) measurement, body composition measurement, and/or a body thickness measurement. In embodiments, the BMD may be calculated by dividing the BMC by the area of bone imaged. During operation of the system 10, in accordance with embodiments of the invention, an x-ray beam with broadband energy levels is utilized to scan the object/patient 12 to image the patient's bones. The acquired scanned images may then be used to diagnose a medical condition such as osteoporosis. In embodiments, the scanned images may be generated in part from determined bone density information acquired during a dual-energy x-ray scan.

Accordingly, and as shown in FIG. 1, the system 10 includes a radiation source 14 operative to emit a radiation beam 16 and to move along a scanning path 18, a radiation detector 20 operative to move along the scanning path 18 and to receive the radiation beam 16, and a controller 22 in electronic communication with the radiation source 14 and the radiation detector 20. As will be described in greater detail below, the controller 22 is operative to regulate the radiation beam 16 while the radiation source 14 and the radiation detector 20 move along the scanning path 18 such that a flux of the radiation beam 16 at the radiation detector 20 is within a target flux range.

In embodiments, the system 10 may further include a patient table 24 for providing a horizontal surface for supporting the patient 12 in a supine or lateral position along a longitudinal axis 26, a support member 28, which in embodiments, may be a C-arm having a lower end 30 and an upper end 32, the lower end 30 being positioned beneath the table 24 so as to support the radiation source 14, and the upper end 32 positioned above the table 24 so as to support the radiation detector 20. While the radiation source 14 and the radiation detector 20 are shown in FIG. 1 as being below and above the patient 12, respectively, it will be understood that the positions of the radiation source 14 and the radiation detector 20 may be reversed such that the radiation source 14 and the radiation detector 20 are above and below the patient 12, respectively. In embodiments, the radiation detector 20 may be fabricated, for example, as a multi-element cadmium-tellurium ("CdTe") detector that provides for energy discrimination. In embodiment, the radiation detector 20 may also be a single or multi-element scintillator with photomultiplication for energy discrimination.

As stated above, the radiation source 14 and the radiation detector 20 move along the scanning path 18 so as to trace a series of transverse scans 34 of the patient 12, during which dual energy radiation, e.g., x-ray, data is collected by the radiation detector 20. In embodiments, the transverse scanning procedure generates either a single scan image or a quantitative data set from a plurality of scanned images acquired across the patient 12, wherein the radiation source 14 and the radiation detector 20 are either longitudinally aligned with the superior-inferior axis of the patient 12 or transversely from one side of patient to another, e.g., left to right. As will be appreciated, scanning the patient 12 using a transverse motion facilitates minimizing the time between acquisitions of adjacent scanned images since the transverse direction across the patient 12 is shorter than the longitudinal direction across the patient 12. Thus, transverse scanning may reduce the severity of motion artifacts between the scanned images, which in turn may further provide for improved accuracy in merging acquired scanned images. As will be appreciated, however, in embodiments, the scanning path 18 may be a series of longitudinal scans.

In certain embodiments, the transverse scanning motion may be produced by actuators (not shown) controlled via a translation controller 36 which may be in electronic communication with, or form part of, the controller 22. During operation, the radiation source 14 produces/generates/emits the radiation beam 16, which in embodiments, may have a fan shape having a plane that is parallel to the longitudinal axis 26. In other embodiments, however, the radiation beam 16 may have a fan shape having a plane that is perpendicular to the longitudinal axis 26. Further, in embodiments, the scanning pattern/path 18 may be configured such that there is some overlap (e.g., 10% of the scanned surface area) between successive scan lines 34 of the radiation beam 16. As will be understood, in embodiments, the radiation beam 16 may have a pencil shape, a cone shape, and/or other shapes appropriate for scanning the patient 12.

In embodiments, the radiation source 14, the radiation detector 20, and the translation controller 36 may be controlled via the controller 22. The controller 22 may electronically communicate with a terminal 38 that includes a display 40, a keyboard 42, and a cursor control device 44, e.g., a mouse, that provide for the input and output of information, e.g., text, images, and/or other forms of data, into and out of the system 10. In embodiments, the controller 22 may be located remotely from the terminal 38. In other embodiments, the controller 22 may be integrated into the terminal 38. In embodiments, the controller 22 is adapted to perform one or more processing operations. For example, the bone and tissue information acquired by the radiation detector 20 may be processed and displayed in real-time during a scanning session as the data is received by the controller 22 from the radiation detector 20. The display 40 may include one or more monitors that present information concerning the patient 12, e.g., the scanned images and bone length images, to the operator for diagnosis and analysis. The displayed images may be modified and the display settings of the display 40 also manually adjusted using the keyboard 42, the mouse 44, and/or a touch screen icon on the display 40.

As will be further understood, the system 10 may be configured to operate in a dual energy mode, a single energy mode, or a broadband mode. In single energy mode, the radiation beam 16 includes a single narrow band of energies, e.g., 20-150 keV. The single energy mode may provide for high resolution scanned images. In dual energy mode, the radiation beam 16 includes two or more narrow bands of energies, which may be emitted simultaneously or in succession. Dual energy mode may be utilized to acquire a scan image of the entire body of the patient 12 that includes information relating to the bones and tissues of the patient's 12 body, which in turn may be utilized to measure bone density and/or other bone and tissue characteristics or content. In broadband mode, the radiation beam 16 may include a single broad band of energies. As will be appreciated, the system 10 may be switchable between the various aforementioned modes.

Figure 2:
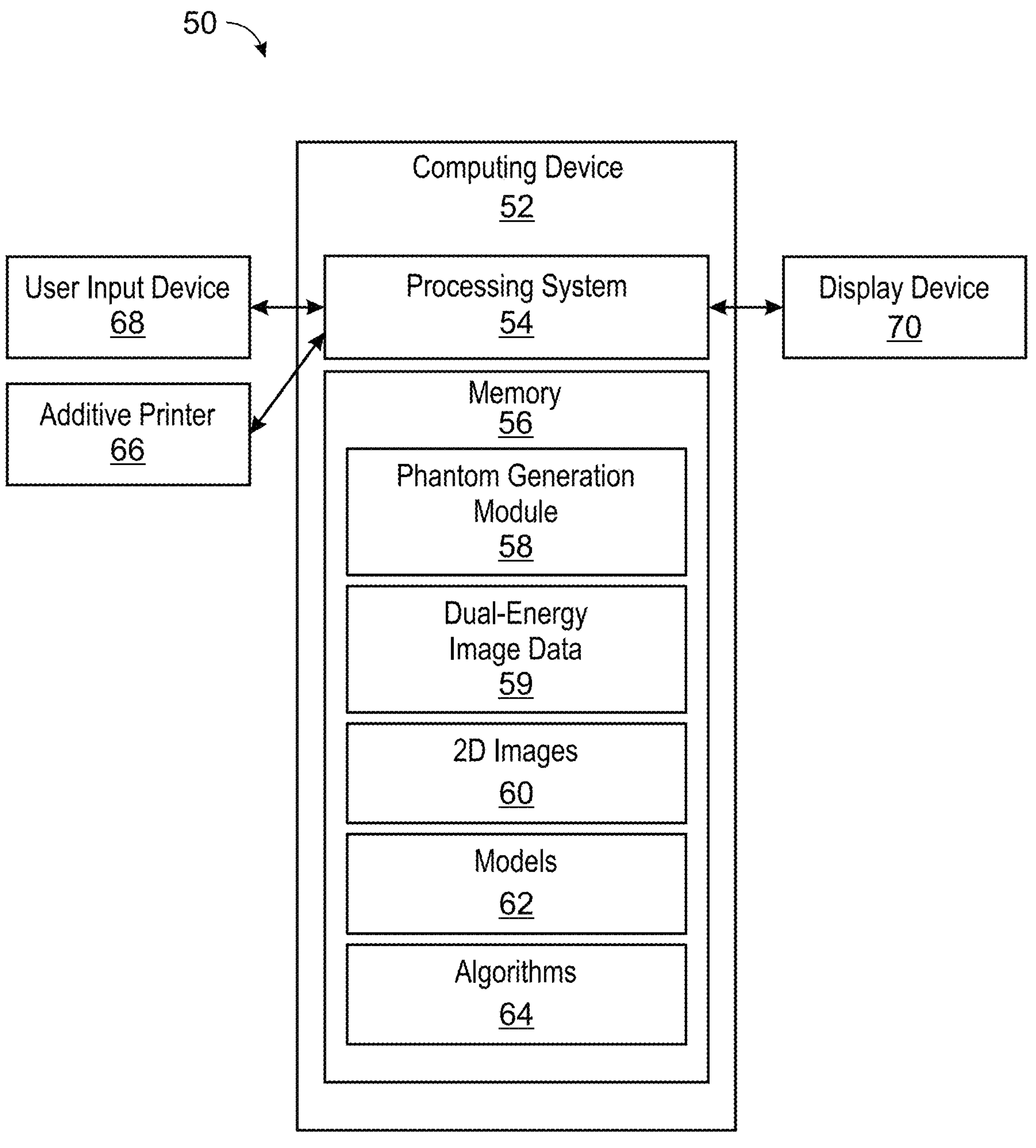
FIG. 2 is a schematic diagram of a system configured for manufacturing an X-ray bone phantom, in accordance with aspects of the present disclosure.

FIG. 2 is a schematic diagram of a system 50 configured for manufacturing an X-ray bone phantom. The X-ray bone phantom is a topographic, semi-anthropomorphic X-ray bone phantom with calibrated attenuation properties. The X-ray bone phantom is made of aluminum. The X-ray bone phantom may be 2D or 3D. The X-ray bone phantom is configured to provide quantitative areal bone mineral density and a realistic projected bone morphology for image quality assessment and lateral distance measurements during calibration. The aluminum of the semi-anthropomorphic X-ray bone phantom is tuned to ensure an X-ray attenuation matches aluminum standards, wherein the aluminum standards were calibrated to areal bone density via dual-energy X-ray absorptiometry.

As depicted, the system 50 includes a computing device 52. The computing device 52 may be located remotely from any medical imaging system. The computing device 52 is configured to obtaining dual-energy scan data from one or more dual-energy scans (e.g., with the system in FIG. 1) of an ex vivo bone phantom. In certain embodiments, the dual-energy scan data may be obtained from one or more patients or subjects. The dual-energy scan data may be from one or more scans of the same ex vivo bone phantom or subject. In certain embodiments, the dual-energy scan data may be from one or more scans of multiple ex vivo bones and/or patients. The computing device 52 is also configured to convert the dual-energy scan data into a two-dimensional image. In certain embodiments, the computing device 52 defines an X-ray projection through the ex vivo bone phantom (or region of interest of subject) based on the dual-energy scan data and calculates (e.g., for each pixel) an aluminum equivalent of attenuating material along the X-ray projection. In certain embodiments, the computing device 52 is configured to convert the dual-energy scan data by generating the two-dimensional image based on a thickness of the aluminum equivalent along the X-ray projection. In certain embodiments, the two-dimensional image is a gray-scale bitmap with an amplitude proportional to the thickness of the aluminum equivalent. In certain embodiments, the two-dimensional image (e.g., gray-scale bitmap) utilized in generating the X-ray bone phantom is an average of a plurality of images respectively generated from the scan of the ex vivo bone phantom or subject. In certain embodiments, the computing device 52 is configured to convert the dual-energy scan data (e.g., from multiple scans of the same ex vivo bone or patient) into a stack of two-dimensional images from which a 3D semi-anthropomorphic X-ray bone phantom can be printed.

The computing device 52 is configured to cause printing, via an additive (3D) printer 66 communicatively coupled to the computing device 52, a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration. In certain embodiments, the semi-anthropomorphic X-ray bone phantom is printed via an additive printer utilizing one or more parameter settings configured to correlate a thickness and a density of the aluminum to mimic bone shape and bone density and related X-ray attenuation. In certain embodiments, the computing device 52 is configured to modify (based on user input) the two-dimensional image to alter the thickness of the aluminum equivalent, wherein the semi-anthropomorphic X-ray bone phantom has one or more features different from the ex vivo bone phantom in morphology and/or areal bone mineral density.

The computing device 52 includes one or more processors forming a processing system 54 configured to execute machine readable instructions stored in non-transitory memory 56. A processor of the processing system 54 may be single core or multi-core, and the programs executed thereon may be configured for parallel or distributed processing. In some embodiments, the processing system 54 may optionally include individual components that are distributed throughout two or more devices, which may be remotely located and/or configured for coordinated processing. In some embodiments, one or more aspects of the processing system 54 may be virtualized and executed by remotely-accessible networked computing devices configured in a cloud computing configuration.

The computing device 52 also includes the non-transitory memory 56. The non-transitory memory 56 may store a phantom generation module 58. The phantom generation module 58 is configured to obtain the dual-energy image data and to generate two dimensional images utilized for additively manufacturing (e.g., printing) the X-ray bone phantoms. The phantom generation module 58 is configured to utilize the dual-energy image data to measure the calcium in the ex vivo bone (or patient) and then determine the aluminum equivalent to utilize in the X-ray bone phantom. The phantom generation module 58 is configured to modify (e.g., via user input) the generated two-dimensional images (e.g., move location of beak). The phantom generation module 58 is configured to generate models for printing 3D models for printing the X-ray bone phantoms. In particular, the phantom generation module 58 is configured to prepare a file (e.g., Standard Tessellation Language or Standard Triangle Language (STL) file) for printing the X-ray bone phantom. The phantom generation module 58 is also configured to edit the STL files and to prepare build files via software (e.g., Magics). The non-transitory memory 56 stores the dual-energy image data 59, the generated two-dimensional images (e.g., gray-scale bitmaps) 60, and the generated models 62 for printing the X-ray bone phantoms. The non-transitory memory 56 may also store various algorithms 64 (e.g., beak-finding algorithm).

In some embodiments, non-transitory memory 56 may include components disposed at two or more devices, which may be remotely located and/or configured for coordinated processing. In some embodiments, one or more aspects of non-transitory memory 56 may include remotely-accessible networked storage devices configured in a cloud computing configuration.

The computing device 52 is communicatively coupled to an additive printer 66 (e.g., 3D printer) that is configured to print the X-ray bone phantoms. The additive printer 66 utilizes one or more parameter settings configured to correlate a thickness and a density of the aluminum to mimic bone shape and bone density and related X-ray attenuation. The computing device 52 provides the files (e.g., models) for printing the X-ray bone phantoms and controls the printing process. The computing device 52 is configured to adjust or alter the printing of the X-ray bone phantom in multiple ways. First way to alter the printing of the X-ray bone phantom is to adjust the printing parameters. The printing parameters may include laser power, layer thickness, scanning/laser speed, hatching/distance between scanning lines, scanning vector/direction, and/or other parameters. The parameters may be utilized to identify the printing process space, design/control X-ray attenuation, and/or to control productivity. The print parameters may be utilized to design the desired density (in the X-ray bone phantoms) with correlation of material thickness to mimic bone shape and density. One or more print parameters (e.g., within one geometry) may be utilized to create the X-ray bone phantom. The print parameters are developed to mimic the result of the X-ray attenuation of bone density. Changing the print parameters enables the control of the density of the material (e.g., aluminum) and impacts X-ray attenuation. In certain embodiments, a combination of different print parameters enables a fine bone density attenuation to be achieved. The second way to alter the printing of the X-ray bone phantom is by modifying the gray-scale bitmap. The third way to alter the printing of the X-ray bone phantom is by averaging many images (e.g., acquired from multiple scans of the same ex vivo bone (or patient)) together in generating the gray-scale bitmap.

User input device 68 may include one or more of a touchscreen, a keyboard, a mouse, a trackpad, a motion sensing camera, or other device configured to enable a user to interact with the computing device 52. In one example, user input device 68 may enable a user to input modifications to gray-scale bitmaps. In another example, user input device 68 may enable a user to input changes to printing parameters.

Display device 70 may include one or more display devices utilizing virtually any type of technology. In some embodiments, the display device 70 may include a computer monitor, and may display the gray-scale bitmaps, STL files, and other information. Display device 70 may be combined with the processing system 54, the non-transitory memory 56, and/or the user input device 68 in a shared enclosure, or may be peripheral display devices and may comprise a monitor, touchscreen, projector, or other display device known in the art, which may enable a user to view data and/or interact with various data stored in the non-transitory memory 56.

Figure 3:
FIG. 3 is a flow chart of a method for manufacturing an X-ray bone phantom, in accordance with aspects of the present disclosure.
Figure 3:
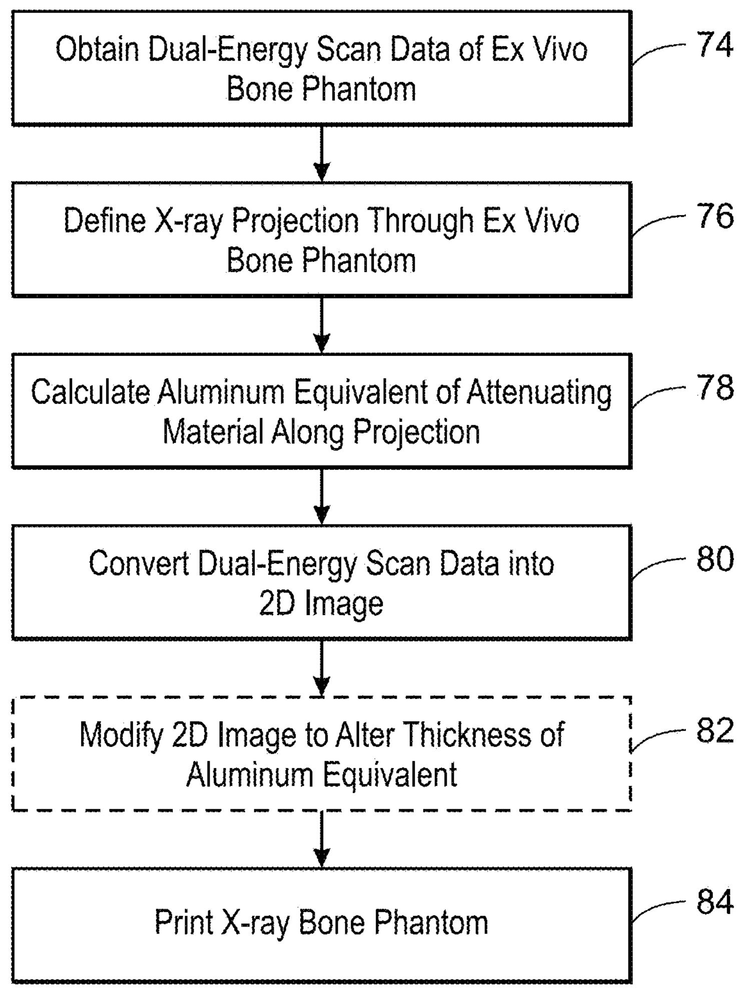

FIG. 3 is a flow chart of a method 72 for manufacturing an X-ray bone phantom. One or more steps of the method 72 may be performed by one or more components of the computing device 52 in FIG. 2.

The method 72 includes obtaining dual-energy scan data from one or more dual-energy scans of an ex vivo bone phantom (or a region of interest of a subject) (block 74). In certain embodiments, the dual-energy image data may be from a single scan of the ex vivo bone phantom (or the region of interest of the subject). In certain embodiments, the dual-energy image data may be from multiple scans of the same ex vivo bone phantom (or same region of interest of the subject). The dual-energy image data may be acquired via scans with a dual-energy imaging system such as the system 10 in FIG. 1. The scans are conducted at highest possible resolution (e.g., 0.3 millimeters by 0.25 millimeters for each image pixel).

The method 72 also includes analyzing the dual-energy image data by defining an X-ray projection through the ex vivo bone phantom (or region of interest of subject) based on the dual-energy scan data (block 76) and calculating (e.g., for each pixel) an aluminum equivalent of attenuating material along the X-ray projection (block 78). The method 72 further includes converting the dual-energy scan data (e.g., analyzed dual-energy image data) into a two-dimensional image (block 80). In certain embodiments, converting the dual-energy scan data into the two-dimensional image includes generating the two-dimensional image based on a thickness of the aluminum equivalent along the X-ray projection. The two-image is a gray-scale bitmap with an amplitude proportional to the thickness of the aluminum equivalent. In certain embodiments (when generating a 3D X-ray bone phantom), the dual-energy scan data is converted into a stack of two-dimensional images. In certain embodiments, the method 72 includes modifying the two-dimensional image (e.g., gray-scale bitmap) to alter the thickness of the aluminum equivalent (block 82). The modification of the two-dimensional image may include moving the location of a beak, removing a beak, or adding a beak. The semi-anthropomorphic X-ray bone phantom generated from the modified two-dimensional image has one or more features different from the ex vivo bone phantom in morphology and/or areal bone mineral density.

The method 72 further includes printing a semi-anthropomorphic X-ray bone phantom (e.g., 2D X-ray bone phantom) made of aluminum based at least on the two-dimensional image (or modified two-dimensional image), wherein the semi-anthropomorphic X-ray bone phantom is configured to provide quantitative areal bone mineral density and a realistic projected bone morphology for image quality assessment and lateral distance measurements during calibration (block 84). In certain embodiments, the semi-anthropomorphic X-ray phantom (e.g., 3D X-ray bone phantom) made of aluminum that is printed is based on stack of two-dimensional images. The aluminum of the semi-anthropomorphic X-ray bone phantom is tuned to ensure an X-ray attenuation matches aluminum standards, wherein the aluminum standards were calibrated to areal bone density via dual-energy X-ray absorptiometry. The semi-anthropomorphic X-ray bone phantom is printed via an additive printer utilizing one or more parameter settings configured to correlate a thickness and a density of the aluminum to mimic bone shape and bone density and related X-ray attenuation.

Figure 4:
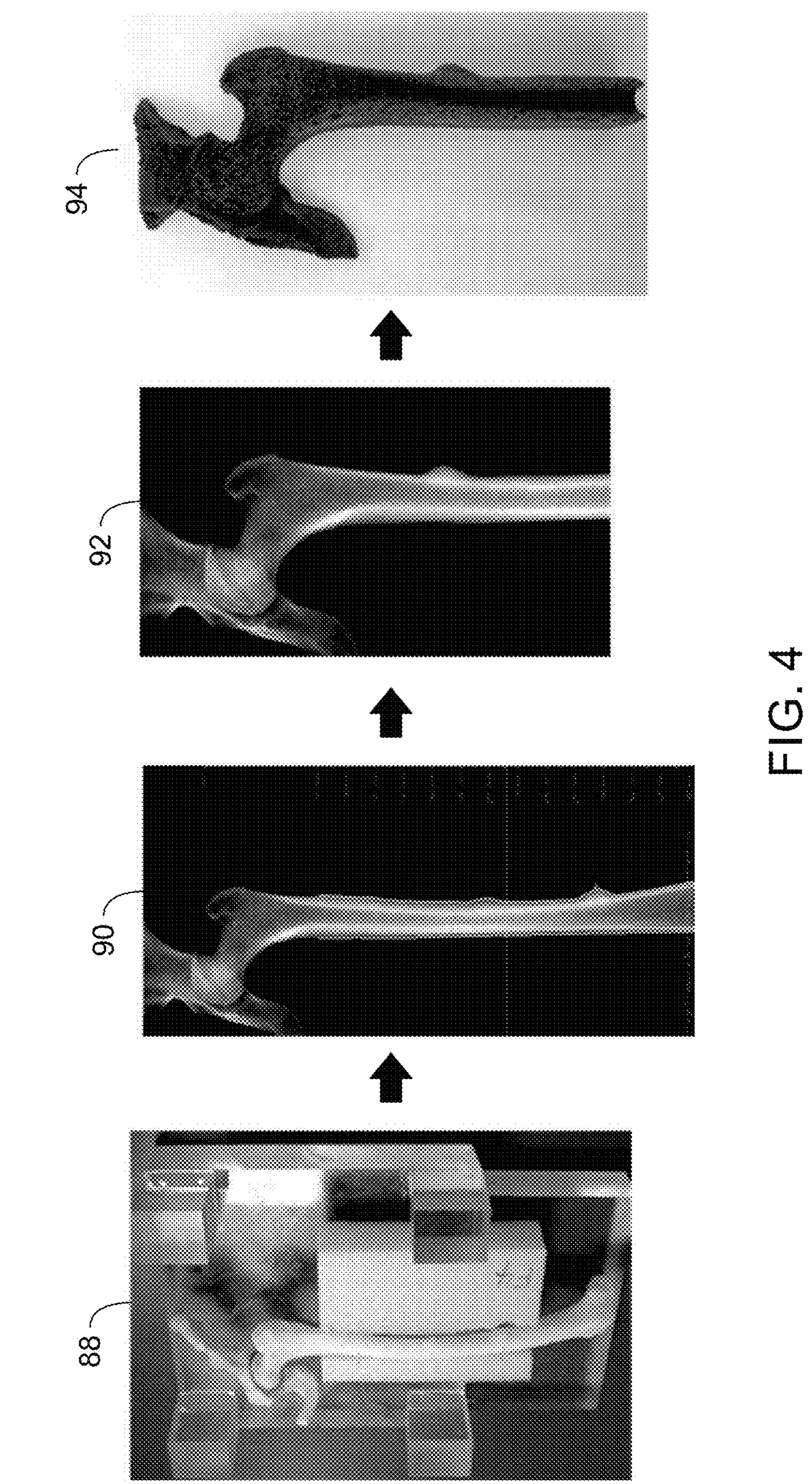
FIG. 4 is a schematic diagram of a process for manufacturing an X-ray bone phantom, in accordance with aspects of the present disclosure.

FIG. 4 is a schematic diagram of a process 86 for manufacturing an X-ray bone phantom. The process 86 includes scanning (e.g., via the system 10 in FIG. 1) an ex vivo bone (shown in image 88) having a calcification on the side at the highest possible resolution multiple times. The ex vivo bone in image 88 is an AFF femur. The process 86 also includes analyzing and averaging the scans and converting this averaged dual-energy scan data to gray-scale bitmap 90. The process 86 further includes modifying the gray-scale bitmap 90 to generate a modified gray-scale bitmap 92. For example, a beak has been cut from its initial location in the gray-scale bitmap 90 to new location or position shown in the gray-scale bitmap 92. The process 86 further includes printing, via an additive printer, the X-ray bone phantom (depicted in image 94) based on the modified gray-scale bitmap 92.

Figure 5:
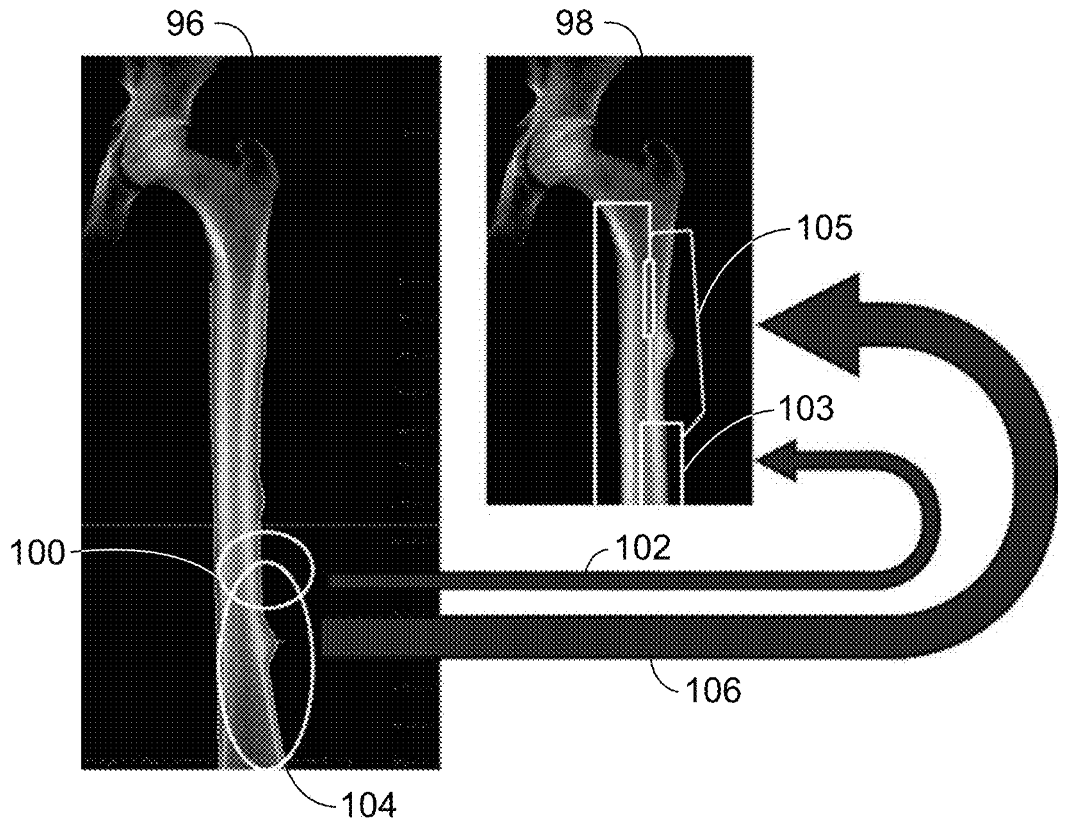
FIG. 5 depicts the modification of a gray-scale bitmap, in accordance with aspects of the present disclosure.

FIG. 5 depicts the modification of a gray-scale bitmap 96. The gray-scale bitmap 96 depicted on the left side of FIG. 5 was generated from dual-energy image data of an ex vivo bone (e.g., femur). The gray-scale bitmap 96 is manipulated to generate gray-scale bitmap 98 depicted on the right side of FIG. 5. First, a portion 100 (lacking a calcification or beak) of the femur in the gray-scale bitmap 96 is moved to a new position as indicated by arrow 102 above its original position to smooth out (i.e., remove any beak or calcification) the area in its new position 103 on the femur as shown in the gray-scale bitmap 98. Second, a portion 104 (having a calcification or beak) of the femur in the gray-scale bitmap 96 is moved to a new position 105 as indicated by arrow 106 to introduce a calcification or beak in its new position on the femur as shown in the gray-scale bitmap 98.

Figure 6:
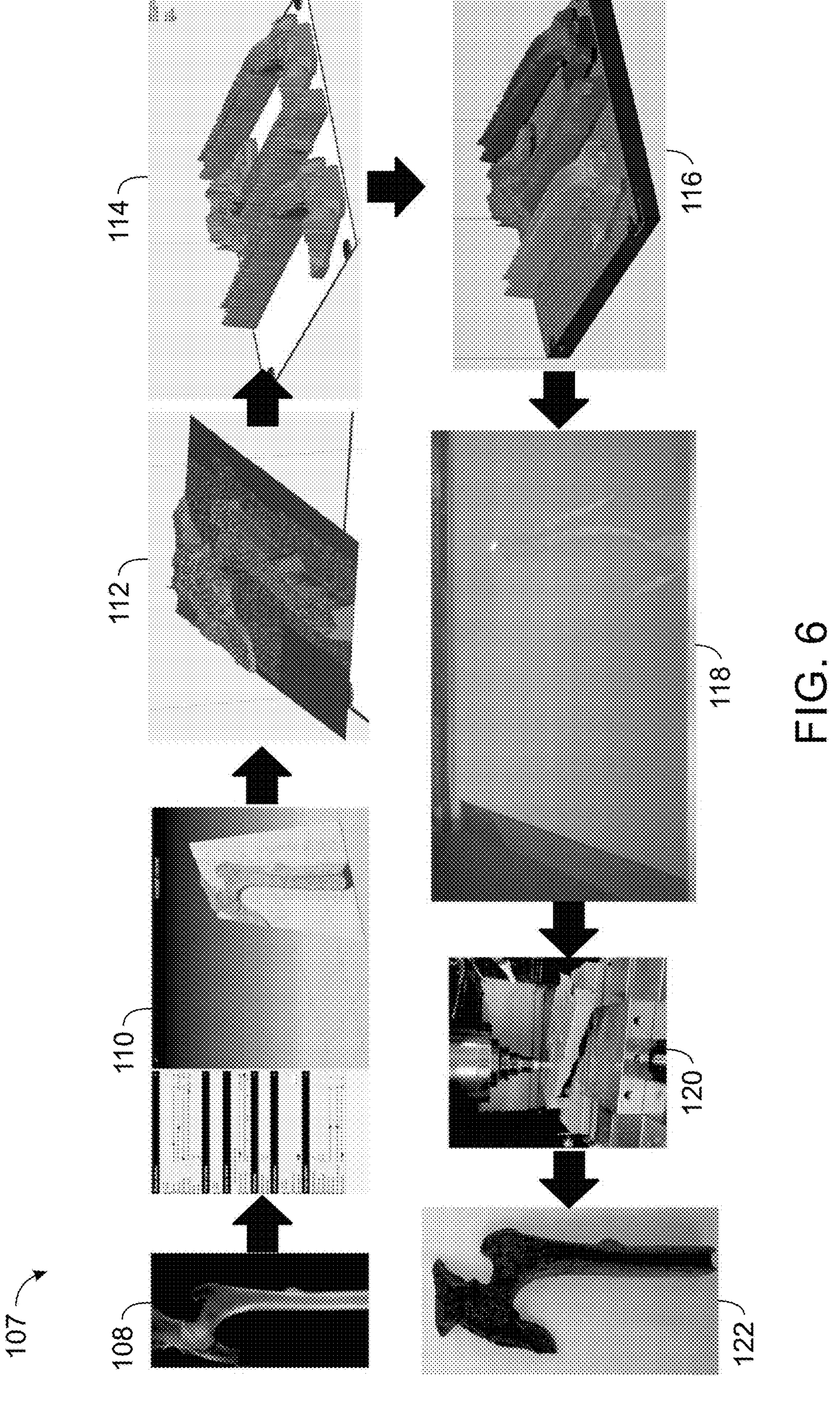
FIG. 6 is a schematic diagram of a more detailed process for manufacturing an X-ray bone phantom, in accordance with aspects of the present disclosure.

FIG. 6 is a schematic diagram of a more detailed process 107 for manufacturing an X-ray one phantom. The process 107 includes preparing from a gray-scale bitmap 108 (e.g., generated from dual-energy image data) of the ex vivo bone an STL file 110 for 3D printing. The process 107 also includes editing the STL files (as indicated by images 112 and 114) and to prepare a build file 116 via software (e.g., Magics). The build file 116 is utilized for the printing process depicted in image 118 to print the X-ray bone phantom. The printing process 118 is similar to that for generating a lithophane. As depicted in image 120, milling may be performed subsequent to the printing process 118 to generate final X-ray bone phantom depicted in image 122.

Figure 7:
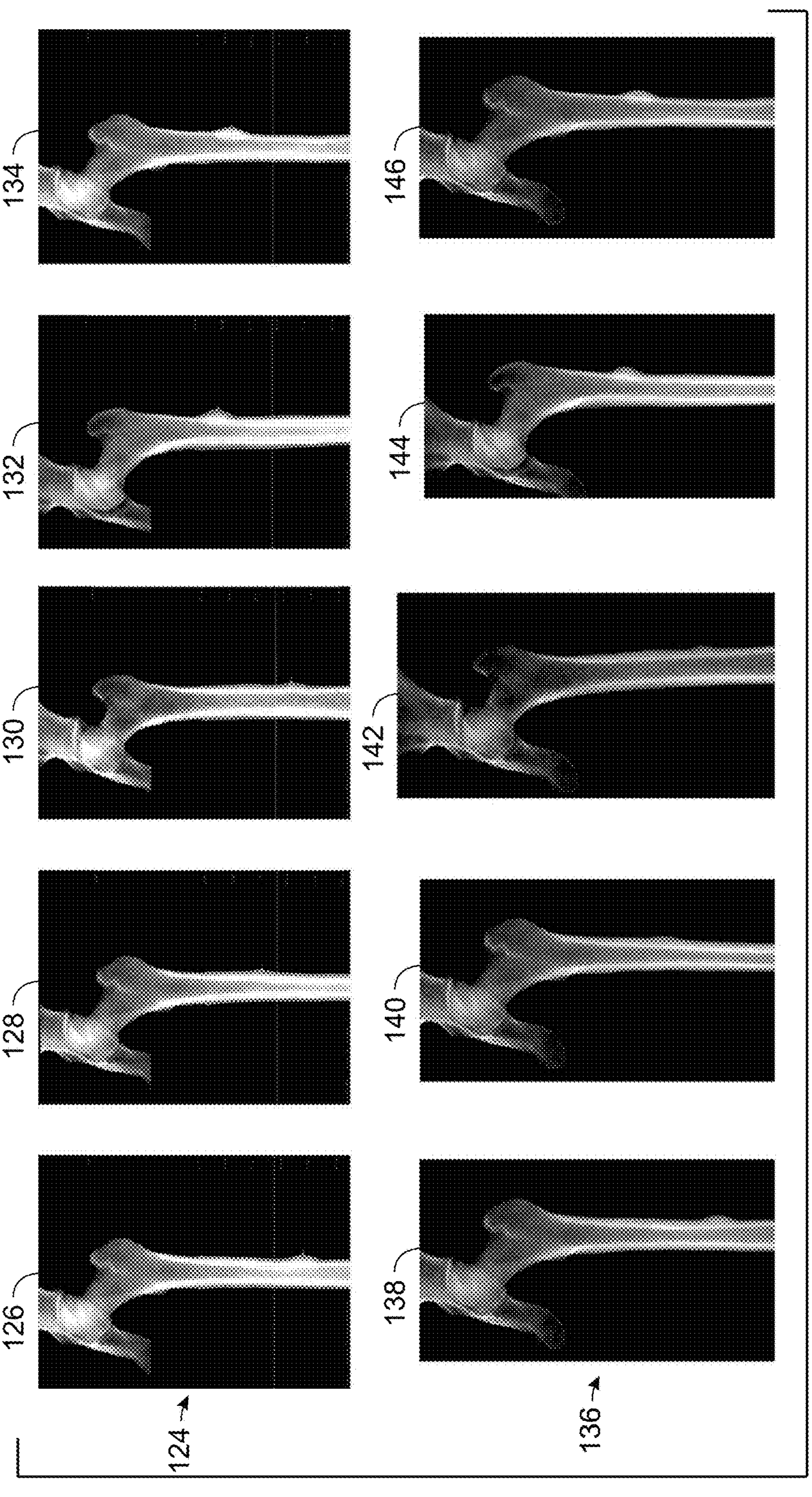
FIG. 7 depicts images of additively manufactured X-ray bone phantoms and ex vivo bone phantoms from which they are derived, in accordance with aspects of the present disclosure.
Figure 8:
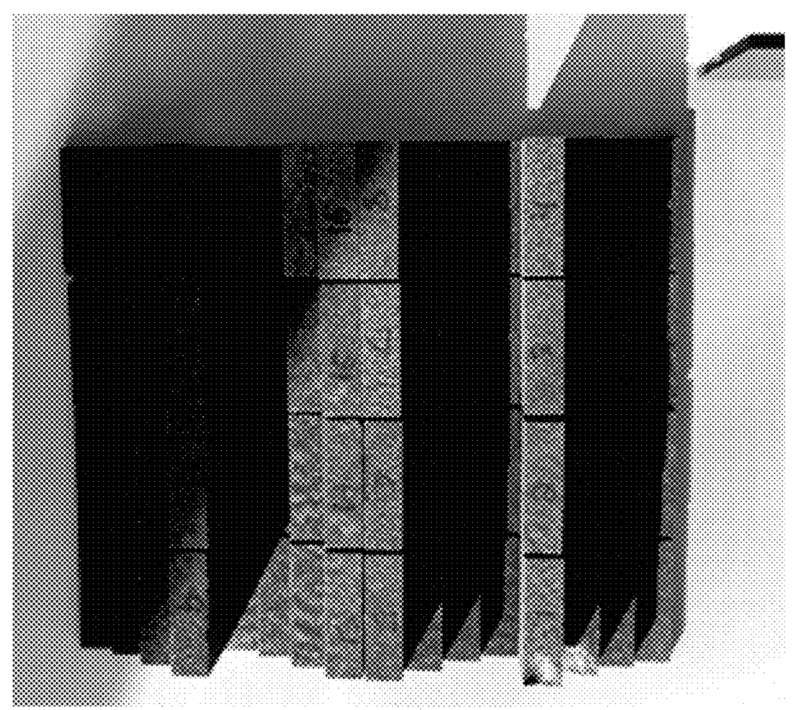
FIG. 8 depicts an image of a top view of a plurality of wedges utilized for calibration, in accordance with aspects of the present disclosure.

FIG. 7 depicts images of additively manufactured X-ray bone phantoms and ex vivo bone phantoms from which they are derived. A top row 124 of FIG. 8 depicts images 126, 128, 130, 132, and 134 of different additively manufactured X-ray bone phantoms acquired with a dual-energy imaging system as described in FIG. 1. A bottom row 136 of FIG. 8 depicts images 138, 140, 142, 144, and 146 of ex vivo bone phantoms (e.g., femurs) with different features. The additively manufactured X-ray bone phantom in image 126 was derived from the ex vivo bone phantom in image 138. The additively manufactured X-ray bone phantom in image 128 was derived from the ex vivo bone phantom in image 140. The additively manufactured X-ray bone phantom in image 130 was derived from the ex vivo bone phantom in image 142. The additively manufactured X-ray bone phantom in image 132 was derived from the ex vivo bone phantom in image 144. The additively manufactured X-ray bone phantom in image 134 was derived from the ex vivo bone phantom in image 146.

Figure 9:
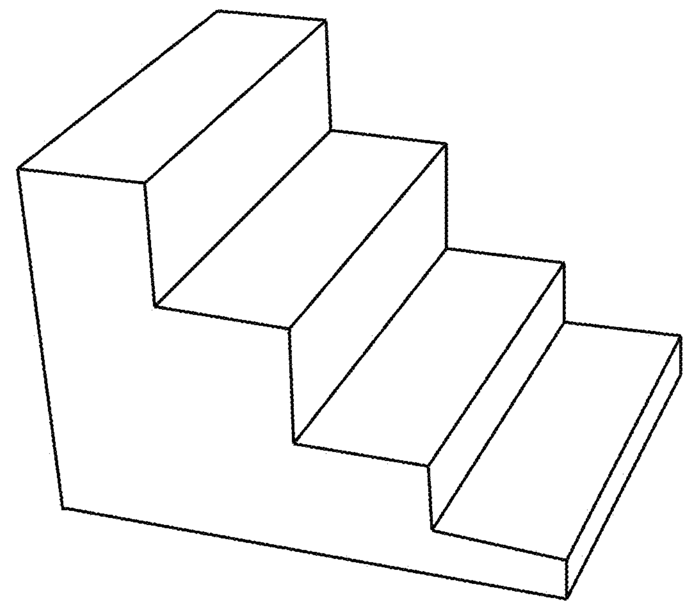
FIG. 9 is a perspective view of a wedge utilized for calibration, in accordance with aspects of the present disclosure.
Figure 10:
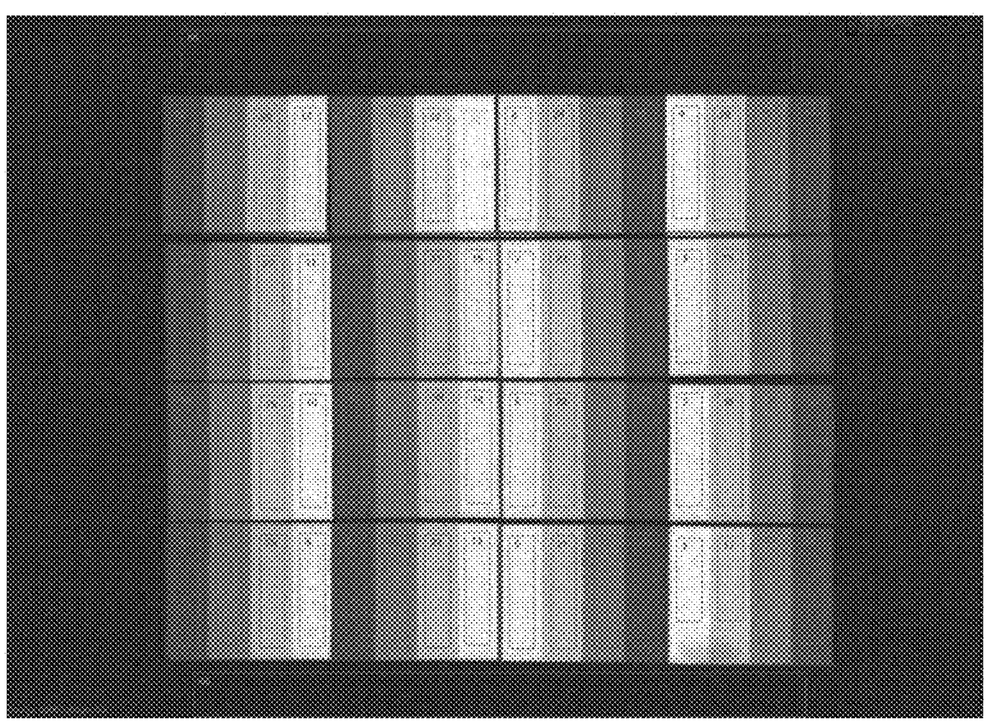
FIG. 10 is a two-dimensional image from DXA scan data of the plurality of wedges in FIG. 8 showing an analysis of pseudo-bone material, in accordance with aspects of the present disclosure.
Figure 11:
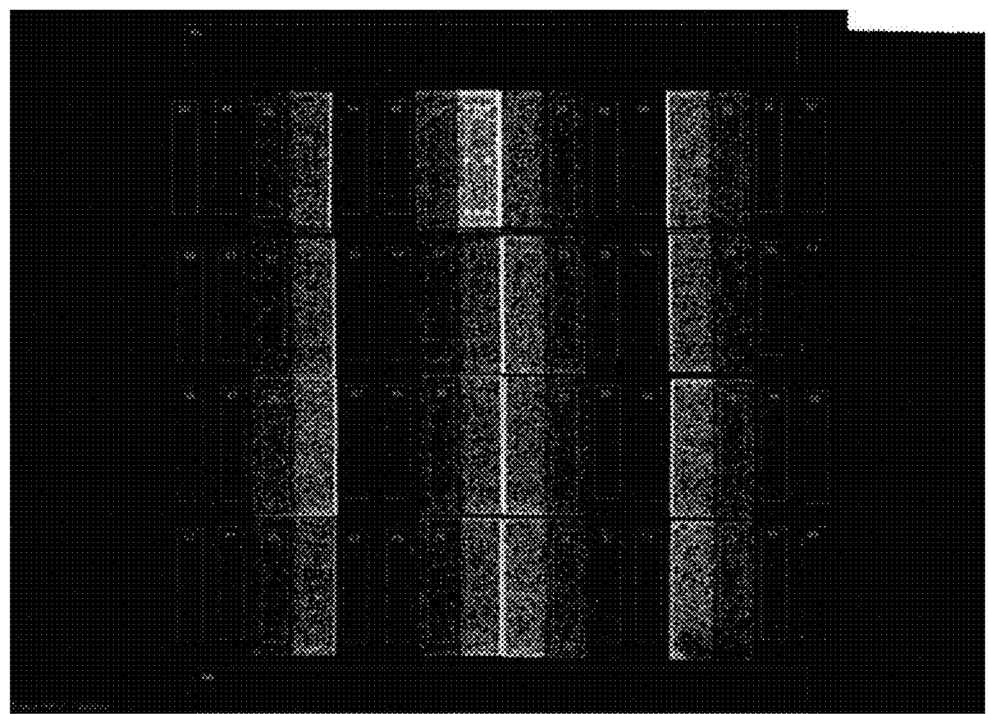
FIG. 11 is a two-dimensional image from DXA scan data of the plurality of wedges in FIG. 8 showing an analysis of pseudo-soft tissue, in accordance with aspects of the present disclosure.
Figure 12:
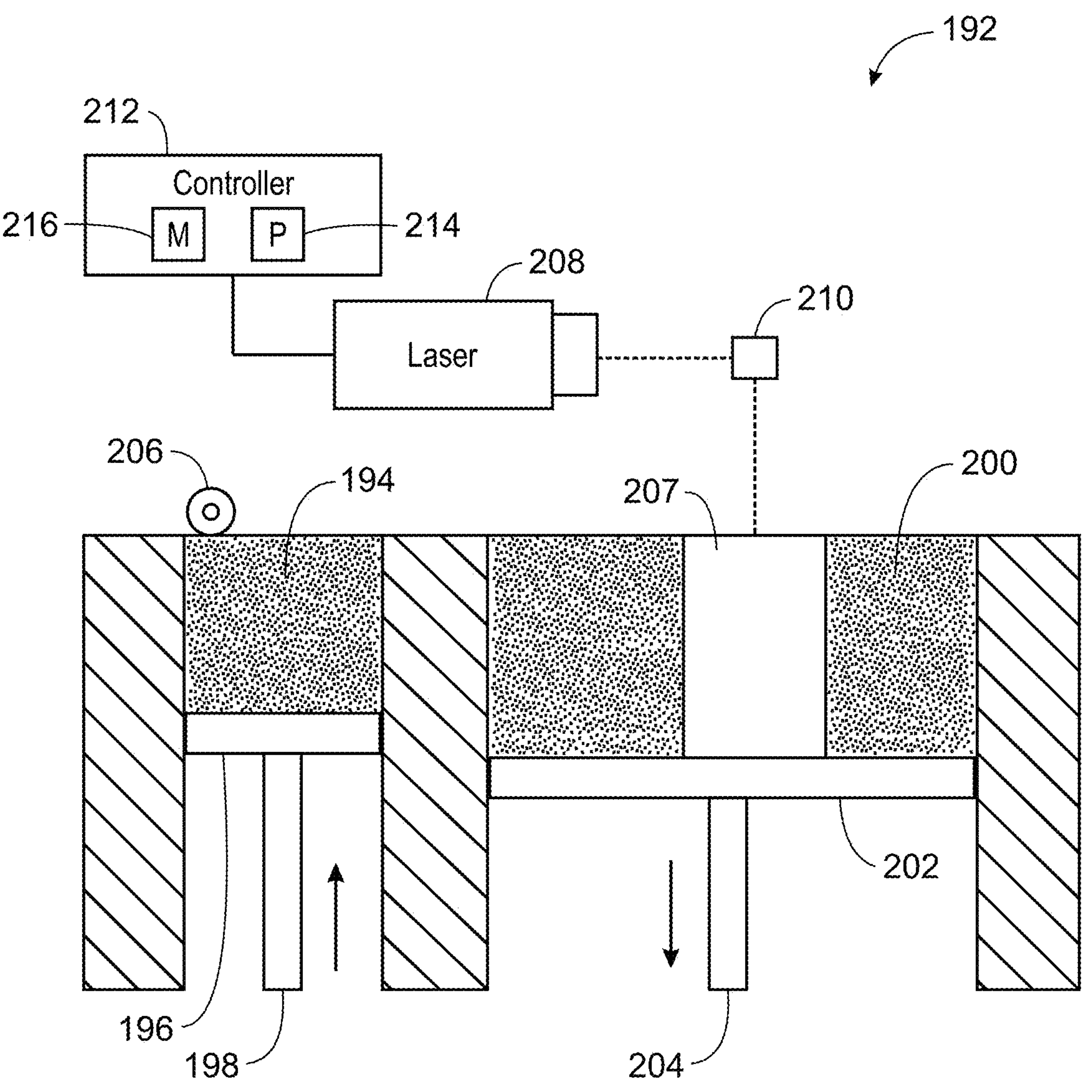
FIG. 12 depicts schematically a laser powder bed fusion system for printing walls or septa of a collimator, in accordance with aspects of the present disclosure.

As mentioned above, an additive printer utilizes one or more parameter settings configured to correlate a thickness and a density of the aluminum to mimic bone shape and bone density and related X-ray attenuation. These parameter settings were determined by utilizing a large number of additive aluminum samples that were made to determine the relationship between X-ray attenuation and various parameters for the additive printer. In particular, sixteen wedges made of additive aluminum are scanned with a calibrated DXA scanner. FIG. 8 depicts an image 148 of a top view of a plurality of wedges 150 (i.e., 16 wedges) utilized for calibration (determining parameter settings). FIG. 9 is a perspective view of a wedge 150. Each wedge 150 is a multi-step wedge of additive aluminum having four steps 152. One of the wedges 150 may be made of additive aluminum with maximum density. The other wedges 150 vary in their additive aluminum density. Each step 152 of each wedge 150 serves as a region of interest that is analyzed. Caliper measurements are obtained of each step height and width. The Al-6061 and acrylic-equivalent is determined of each additive aluminum fine-tuned step of the wedges 150. FIG. 10 is a two-dimensional image 154 from DXA scan data of the sixteen wedges 150 showing the analysis of pseudo-bone material (PBM) (i.e., centimeters (cm) of AL-6061). FIG. 11 is a two-dimensional image 156 from DXA scan data of the sixteen wedges 150 showing the analysis of pseudo-soft tissue (PST) (i.e., centimeters (cm) of acrylic equivalence). The results of the analysis of the sixteen wedges 150 was additive aluminum areal density ranges from 63 percent to 88 percent of AL-6061. The result of the analysis of the sixteen wedges was equivalent acrylic area density of 0.012 to 0.030 acrylic-cm per additive-cm.

The X-ray bone phantom may be 3D printed utilizing LPBF. LPBF is also known as direct metal laser sintering (DMLS), selective laser melting (SLM) or direct metal printing (DMP). FIG. 14 depicts schematically an LPBF system 192 for printing an X-ray bone phantom. The LPBF system 192 includes a metal powder stock 194 (e.g., of aluminum powder) located on a powder platform 196 coupled to a piston 198. The LPBF system 192 also includes a powder bed 200 (e.g. having aluminum powder) located on a build platform 202 coupled to a piston 204. The LPBF system 192 further includes a powder roller 206 to transfer (e.g., spread) powder from the powder stock 194 to the powder bed 200 in between the formation of the layers of the X-ray bone phantom 207. The LPBF system 192 still further includes a laser 208 that may direct a laser via mirror 210 or directly onto powder bed 200 to form the layers of the X-ray bone phantom 207.

The LPBF system 192 still further includes a controller 212 coupled to the laser 208. The controller 212 includes include a processor 214 (e.g., processing circuitry) and memory 216 (e.g., memory circuitry). The processor 214 may include multiple microprocessors, one or more "general-purpose" microprocessors, one or more special-purpose microprocessors, and/or one or more application specific integrated circuits (ASICS), system-on-chip (SoC) device, or some other processor configuration. For example, the processor 214 may include one or more reduced instruction set (RISC) processors or complex instruction set (CISC) processors. These instructions may be encoded in programs or code stored in a tangible non-transitory computer-readable medium (e.g., an optical disc, solid state device, chip, firmware, etc.) such as the memory 216. The controller 212 controls the operation of the laser 208 and the LPBF system 192.

To form the X-ray bone phantom 207, a layer of powder (e.g., aluminum powder) is spread over the build platform 202 (e.g., via the powder roller 206). The laser 208 fuses this first layer of the X-ray bone phantom 207. A new layer of powder is then spread across the previous layer (e.g., via the powder roller 206) and a further layer is fused and added on the initial layer. This process repeats until the entire X-ray bone phantom 207 is formed. Then the loose, unfused powder is removed during post-processing.

Technical effects of the disclosed embodiments include eliminating the use of ex vivo bone phantoms, which is desirable for both ethical and practical reasons (fragility of bones). Technical effects of the disclosed embodiments include reducing the cost associated with manufacturing X-ray bone phantoms. Technical effects of the disclosed embodiments include providing a phantom that is easier to control and to handle compared to ex vivo bone phantoms. Technical effects of the disclosed embodiments include providing an X-ray bone phantom with truly anthropomorphic attenuation properties at a fine scale. Technical effects of the disclosed embodiments include enabling the manufacture of unique X-ray bone phantoms that can be utilized to verify device performance for rare, outlier conditions.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The disclosure also provides support for a computer-implemented method, comprising: obtaining, via a processing system comprising one or more processors, dual-energy scan data from one or more dual-energy scans of an ex vivo bone phantom; converting, via the processing system, the dual-energy scan data into a two-dimensional image; and printing, via the processing system, a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration. In a first example of the computer-implemented method, the aluminum of the semi-anthropomorphic X-ray bone phantom is tuned to ensure an X-ray attenuation matches aluminum standards, wherein the aluminum standards were calibrated to areal bone density via dual-energy X-ray absorptiometry. In a second example of the computer-implemented method, optionally including the first example, the semi-anthropomorphic X-ray bone phantom is printed via an additive printer utilizing one or more parameter settings configured to correlate a thickness and a density of the aluminum to mimic bone shape and bone density and related X-ray attenuation. In a third example of the computer-implemented method, optionally including one or both of the first and second examples, the computer-implemented method further comprises defining, via the processing system, an X-ray projection through the ex vivo bone phantom based on the dual-energy scan data and calculating, via the processing system, an aluminum equivalent of attenuating material along the X-ray projection. In a fourth example of the computer-implemented method, optionally including one or more or each of the first through third examples, converting the dual-energy scan data into the two-dimensional image comprises generating the two-dimensional image based on a thickness of the aluminum equivalent along the X-ray projection. In a fifth example of the computer-implemented method, optionally including one or more or each of the first through fourth examples, the two-dimensional image comprises a gray-scale bitmap with an amplitude proportional to the thickness of the aluminum equivalent. In a sixth example of the computer-implemented method, optionally including one or more or each of the first through fifth examples, the computer-implemented method further comprises modifying, via the processing system, the two-dimensional image to alter the thickness of the aluminum equivalent, wherein the semi-anthropomorphic X-ray bone phantom has one or more features different from the ex vivo bone phantom in morphology and/or areal bone mineral density. In a seventh example of the computer-implemented method, optionally including one or more or each of the first through sixth examples, the semi-anthropomorphic X-ray bone phantom is two-dimensional. In an eighth example of the computer-implemented method, optionally including one or more or each of the first through eighth examples, the computer-implemented method further comprises converting, via the processing system, the dual-energy scan data into a stack of two-dimensional images; and printing, via the processing system, the semi-anthropomorphic X-ray bone phantom made of aluminum based on the stack of two-dimensional images, wherein the semi-anthropomorphic X-ray bone phantom is three-dimensional.

The disclosure also provides support for a system manufacturing an X-ray bone phantom, comprising: a memory encoding processor-executable routines; and a processing system comprising one or more processors and configured to access the memory and to execute the processor-executable routines, wherein the processor-executable routines, when executed by the processing system, cause the processing system to: obtain dual-energy scan data from one or more dual-energy scans of an ex vivo bone phantom; convert the dual-energy scan data into a two-dimensional image; and print a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration. In a first example of the system, the aluminum of the semi-anthropomorphic X-ray bone phantom is tuned to ensure an X-ray attenuation matches aluminum standards, wherein the aluminum standards were calibrated to areal bone density via dual-energy X-ray absorptiometry. In a second example of the system, optionally including the first example, the semi-anthropomorphic X-ray bone phantom is printed via an additive printer utilizing one or more parameter settings configured to correlate a thickness and a density of the aluminum to mimic bone shape and bone density and related X-ray attenuation. In a third example of the system, optionally including one or both of the first and second examples, the processor-executable routines, when executed by the processing system, further cause the processing system to define an X-ray projection through the ex vivo bone phantom based on the dual-energy scan data and calculating, via the processing system, an aluminum equivalent of attenuating material along the X-ray projection. In a fourth example of the system, optionally including one or more or each of the first through third examples, converting the dual-energy scan data into the two-dimensional image comprises generating the two-dimensional image based on a thickness of the aluminum equivalent along the X-ray projection. In a fifth example of the system, optionally including one or more or each of the first through fourth examples, the two-dimensional image comprises a gray-scale bitmap with an amplitude proportional to the thickness of the aluminum equivalent. In a sixth example of the system, optionally including one or more or each of the first through fifth examples, the processor-executable routines, when executed by the processing system, further cause the processing system to modify the two-dimensional image to alter the thickness of the aluminum equivalent, wherein the semi-anthropomorphic X-ray bone phantom has one or more features different from the ex vivo bone phantom in morphology and/or areal bone mineral density. In a seventh example of the system, optionally including one or more or each of the first through sixth examples, the semi-anthropomorphic X-ray bone phantom is two-dimensional. In an eighth example of the system, optionally including one or more or each of the first through seventh examples, the processor-executable routines, when executed by the processing system, further cause the processing system to: convert the dual-energy scan data into a stack of two-dimensional images; and print the semi-anthropomorphic X-ray bone phantom made of aluminum based the stack of two-dimensional images, wherein the semi-anthropomorphic X-ray bone phantom is three-dimensional.

The disclosure also provides support for a non-transitory computer-readable medium, the non-transitory computer-readable medium comprising processor-executable code that when executed by a processing system comprising one or more processors, causes the processing system to: obtain dual-energy scan data from one or more dual-energy scans of an ex vivo bone phantom; convert the dual-energy scan data into a two-dimensional image; and print a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration. In a first example of the non-transitory computer-readable medium, the aluminum of the semi-anthropomorphic X-ray bone phantom is tuned to ensure an X-ray attenuation matches aluminum standards, wherein the aluminum standards were calibrated to areal bone density via dual-energy X-ray absorptiometry.

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for manufacturing an X-ray bone phantom, comprising:

obtaining, via a processing system comprising one or more processors, dual-energy scan data from one or more dual-energy scans of an ex vivo bone phantom;

converting, via the processing system, the dual-energy scan data into a two-dimensional image; and printing, via the processing system, a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

2. The computer-implemented method of claim 1, wherein the aluminum of the semi-anthropomorphic X-ray bone phantom is tuned to ensure an X-ray attenuation matches aluminum standards, wherein the aluminum standards were calibrated to areal bone density via dual-energy X-ray absorptiometry.

3. The computer-implemented method of claim 2, wherein the semi-anthropomorphic X-ray bone phantom is printed via an additive printer utilizing one or more parameter settings configured to correlate a thickness and a density of the aluminum to mimic bone shape and bone density and related X-ray attenuation.

4. The computer-implemented method of claim 1, further comprising defining, via the processing system, an X-ray projection through the ex vivo bone phantom based on the dual-energy scan data and calculating, via the processing system, an aluminum equivalent of attenuating material along the X-ray projection.

5. The computer-implemented method of claim 4, wherein converting the dual-energy scan data into the two-dimensional image comprises generating the two-dimensional image based on a thickness of the aluminum equivalent along the X-ray projection.

6. The computer-implemented method of claim 5, wherein the two-dimensional image comprises a gray-scale bitmap with an amplitude proportional to the thickness of the aluminum equivalent.

7. The computer-implemented method of claim 5, further comprising modifying, via the processing system, the two-dimensional image to alter the thickness of the aluminum equivalent, wherein the semi-anthropomorphic X-ray bone phantom has one or more features different from the ex vivo bone phantom in morphology and/or areal bone mineral density.

8. The computer-implemented method of claim 1, further comprising:

converting, via the processing system, the dual-energy scan data into a stack of two-dimensional images; and printing, via the processing system, the semi-anthropomorphic X-ray bone phantom made of aluminum based on the stack of two-dimensional images, wherein the semi-anthropomorphic X-ray bone phantom is three-dimensional.

9. A system for manufacturing an X-ray bone phantom, comprising:

a memory encoding processor-executable routines; and a processing system comprising one or more processors and configured to access the memory and to execute the processor-executable routines, wherein the processor-executable routines, when executed by the processing system, cause the processing system to:

obtain dual-energy scan data from one or more dual-energy scans of an ex vivo bone phantom;

convert the dual-energy scan data into a two-dimensional image; and print a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

10. The system of claim 9, wherein the aluminum of the semi-anthropomorphic X-ray bone phantom is tuned to ensure an X-ray attenuation matches aluminum standards, wherein the aluminum standards were calibrated to areal bone density via dual-energy X-ray absorptiometry.

11. The system of claim 10, wherein the semi-anthropomorphic X-ray bone phantom is printed via an additive printer utilizing one or more parameter settings configured to correlate a thickness and a density of the aluminum to mimic bone shape and bone density and related X-ray attenuation.

12. The system of claim 9, wherein the processor-executable routines, when executed by the processing system, further cause the processing system to define an X-ray projection through the ex vivo bone phantom based on the dual-energy scan data and calculating, via the processing system, an aluminum equivalent of attenuating material along the X-ray projection.

13. The system of claim 12, wherein converting the dual-energy scan data into the two-dimensional image comprises generating the two-dimensional image based on a thickness of the aluminum equivalent along the X-ray projection.

14. The system of claim 13, wherein the two-dimensional image comprises a gray-scale bitmap with an amplitude proportional to the thickness of the aluminum equivalent.

15. The system of claim 13, wherein the processor-executable routines, when executed by the processing system, further cause the processing system to modify the two-dimensional image to alter the thickness of the aluminum equivalent, wherein the semi-anthropomorphic X-ray bone phantom has one or more features different from the ex vivo bone phantom in morphology and/or areal bone mineral density.

16. The system of claim 9, wherein the processor-executable routines, when executed by the processing system, further cause the processing system to:

convert the dual-energy scan data into a stack of two-dimensional images; and print the semi-anthropomorphic X-ray bone phantom made of aluminum based on the stack of two-dimensional images, wherein the semi-anthropomorphic X-ray bone phantom is three-dimensional.

17. A non-transitory computer-readable medium, the non-transitory computer-readable medium comprising processor-executable code that when executed by a processing system comprising one or more processors, causes the processing system to:

obtain dual-energy scan data from one or more dual-energy scans of an ex vivo bone phantom;

convert the dual-energy scan data into a two-dimensional image; and print a semi-anthropomorphic X-ray bone phantom made of aluminum based at least on the two-dimensional image, wherein the semi-anthropomorphic X-ray bone phantom is configured to provide quantitative areal bone mineral density and a realistic projected bone morphology for image quality assessment and lateral distance measurements during calibration.

18. The non-transitory computer-readable medium of claim 17, wherein the aluminum of the semi-anthropomorphic X-ray bone phantom is tuned to ensure an X-ray attenuation matches aluminum standards, wherein the aluminum standards were calibrated to areal bone density via dual-energy X-ray absorptiometry.

* * * * *